United States Patent [19]

Schwender et al.

[11] 4,250,177
[45] Feb. 10, 1981

[54] SUBSTITUTED 10-OXO-10H-PYRIDAZINO(6,1-b)QUINAZOLINE-2-CARBOXYLIC ACIDS

[75] Inventors: Charles F. Schwender, Dexter, Mich.; Brooks R. Sunday, Hackettstown, N.J.

[73] Assignee: Warner-Lambert Company, Morris Plains, N.J.

[21] Appl. No.: 113,849

[22] Filed: Jan. 21, 1980

Related U.S. Application Data

[63] Continuation-in-part of Ser. No. 968,656, Dec. 11, 1978, abandoned.

[51] Int. Cl.³ .................. A61K 31/505; C07D 487/04
[52] U.S. Cl. ................................. 424/250; 544/233; 544/234
[58] Field of Search ................. 544/233, 234; 424/250

[56] References Cited

PUBLICATIONS

Beyer et al., I, Chem. Abs. 60, 9276g (1934).
Yanai et al., I, Chem. Abs. 63, 5638c (1965).
Beyer et al., II, Chem. Abs. 56, 5955c (1961).
Arya et al., Ind. J. Chem. 14B, 879–882 (1976).
Ghelardoni et al., Ann. d: Chimira 64, 445–453 (1974).
Chem. Abs., 8th Coll. Index, p. 264445.
Yanai et al., II, Chem. Abs. 70, 4034y (1968).

*Primary Examiner*—Mark L. Berch
*Attorney, Agent, or Firm*—Walter Patton; Stephen Raines; Albert Graddis

[57] ABSTRACT

The invention relates to substituted 10-oxo-10H-pyridazino(6,1-b)quinazoline-2-carboxylic acids having the formula:

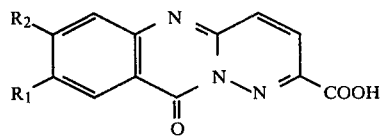

wherein $R_1$ is hydrogen, halogen; $R_2$ is hydrogen, lower alkyl containing one to three carbon atoms, or wherein $R_1$ and $R_2$ taken together with the carbon atoms to which they are attached in a benzo ring, and the pharmaceutically acceptable salts thereof. These compounds are useful as anti-allergic agents.

7 Claims, No Drawings

SUBSTITUTED 10-OXO-10H-PYRIDAZINO(6,1-b)QUINAZOLINE-2-CARBOXYLIC ACIDS

This is a continuation-in-part of copending U.S. Ser. No. 968,656, filed Dec. 11, 1978, now abandoned.

SUMMARY AND DETAILED DESCRIPTION

The invention relates to substituted 10-oxo-10H-pyridazino(6,1-b)quinazoline-2-carboxylic acids which are anti-allergic agents having the formula:

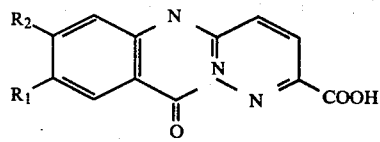

wherein $R_1$ is hydrogen, halogen; $R_2$ is hydrogen, lower alkyl containing one to three carbon atoms, or wherein $R_1$ and $R_2$ taken together with the carbon atoms to which they are attached is a benzo ring, and the pharmaceutically acceptable salts thereof. As used in the above definition the term halogen includes fluorine, chlorine and bromine.

The preferred compounds of the invention are 7-methyl-10-oxo-10H-pyridazino(6,1-b)quinazoline-2-carboxylic acid; 8-chloro-10-oxo-10H-pyridazino(6,1-b)quinazoline-2-carboxylic acid; 10-oxo-10H-pyridazino-(6,1-b)quinazoline-2-carboxylic acid; 12-oxo-12H-benzo(g)pyridazino(6,1-b)quinazoline-2-carboxylic acid; and the pharmaceutically acceptable salts thereof.

The preferred compounds encompassed by the invention, along with their melting points expressed in degrees centigrade and pharmacological data may be found in the following Table:

| No. | R 1 | R 2 | Mp°C. dec | % Inhibition Rat PCA Test 0.5 mg/kg iv |
|---|---|---|---|---|
| 1 | —Cl | H | 260–62 | 91 |
| 2 | H | H | 239–43 | 76 |
| 3 | 7,8-(—CH=CH—CH=CH—) | | 264–66 | 36 |
| 4 | H | —CH$_3$ | 246–49 | 32 |
| 5 | Cromolyn Sodium (Fisons) | | | 50% at 1.5 mg/kg iv |

In another aspect of the invention there is provided a pharmaceutical composition comprising a compound of Formula I as has been defined or a pharmaceutically acceptable salt thereof together with any of the conventional pharmaceutically acceptable carriers or excipients.

The pharmaceutically acceptable salts of the compounds of general Formula I may be prepared by conventional reactions with equivalent amounts of organic or inorganic acids and bases. As exemplary, but not limiting, of pharmaceutically acceptable salts are the salts of hydrochloric, hydrobromic, sulfuric, benzenesulfonic, acetic, fumaric, malic and citric acids, and appropriate bases such as the hydroxides or bicarbonates of potassium and sodium.

The pharmaceutical compositions may be administered parenterally in combination with conventional injectable liquid carriers such as sterile pyrogen-free water, sterile peroxide-free ethyl oleate, dehydrated alcohol or propylene glycol. Conventional pharmaceutical adjuvants for injection solutions such as stablizing agents, solubilizing agents and buffers, complex forming agents such as ethylenediaminetetraacetic acid, tartrate and citrate buffers and highmolecular weight polymers such as polyethylene oxide for viscosity regulation may be added. Such compositions may be injected intramuscularly, intraperitoneally, or intravenously.

The pharmaceutical compositions may also be formulated into orally administratable compositions containing one or more physiologically compatible carriers or excipients and may be solid or liquid in form. These compositions may, if desired, contain conventional ingredients such as binding agents, for example, syrups, acacia, gelatin, sorbitol, tragacanth, or polyvinylpyrrolidone; fillers, for example, lactose, mannitol, starch, calcium phosphate, sorbitol or methylcellulose; lubricants, for example, magnesium stearate, high-molecular weight polymers such as polyethylene glycols, high-molecular weight fatty acids such as stearic acid or silica; disintegrants, for example, starch; acceptable wetting agents as, for example, sodium lauryl sulfate. These compositions may take any convenient form, for example, tablets, capsules, lozenges, aqueous or oily suspensions, emulsions, or dry products suitable for reconstitution with water or other liquid medium before use. The liquid oral forms of administration may, of course, contain flavors; sweeteners; preservatives, for example, methyl or propyl p-hydroxybenzoates; suspending agents, for example, sorbitol, glucose or other sugar syrup, methyl, hydroxmethyl, or carboxymethyl celluloses, or gelatin; emulsifying agents as, for example, lecithin or sorbitan monooleate; or thickening agents. Non-aqueous compositions may also be formulated which comprise edible oils as, for example, fishliver or vegetable oils. These liquid compositions may conveniently be encapsulated in, for example, gelatin capsules in a unit dosage amount.

The pharmaceutical compositions may also be administered topically as an aerosol spray directly on the reaction site or systemically into the lungs.

A particular aspect of this invention comprises a compound of formula I in an effective unit dose form. By "effective unit dose" is meant a predetermined amount sufficient to be effective to bring about the desired anti-allergic effect.

The passive cutaneous anaphylaxis PCA procedure shows the compounds of the invention to inhibit the allergic response of presensitized rats. The results of this testing may be seen in the preceding table. This procedure is discussed in detail in U.S. Pat. No. 4,028,383 to Brown and Unangst and U.S. Pat. No. 4,076,720 to Connor, Young and von Strandtmann.

The compounds of the invention are useful in the prevention of allergic and asthmatic reactions in mammals. For example, in tests conducted by the procedures outlined in the Brown and Connor patents noted above, these compounds are capable of inhibiting allergic reactions in mammals at a dose level of 0.1 to 10.0 mg/kg of body weight when administered intravenously or systemically by inhalation areosol. Acordingly, these compounds are indicated in the management of allergic conditions such as bronchial asthma.

In yet a further aspect of the invention there is provided a method of producing an anti-allergic effect in mammals, including man, which comprises the administration if an effective anti-allergic amount of a compound of formula I or a pharmaceutically acceptable salt thereof.

The dosage of the compounds of formula I or their pharmaceutically acceptable salts depends, of course, on the nature and severity of the biological reaction to be countered, as well as the path of administration.

The invention is illustrated by the following examples.

EXAMPLE 1

General Methods of Preparation of Substituted 10-oxo-10H-pyridazino(6,1-b)quinazolines.

PROCEDURE A

An appropriately substituted chloropyridazine is reacted with either an appropriately substituted anthranilic acid or anthranilate ester in an acidic refluxing medium to give the desired product. The acidic medium may be, for example, acetic acid.

PROCEDURE B

A mixture of the appropriately substituted anthranilic acid, appropriately substituted 3-chloropyridazine and an alcohol, such as ethyl alcohol, containing an acid, such as hydrochloric acid, is heated at reflux temperature to give the desired product.

PROCEDURE C

A mixture of the appropriately substituted anthranilate ester and the appropriately substituted 3-chloropyridazine is heated at 100°–225° C. to give the desired product.

EXAMPLE 2

8-chloro-10-oxo-10H-pyridazino(6,1-b)quinazoline-2-carboxylic acid.

A mixture of 5-chloroanthralinic acid (5.4 g, 31.6 mmol) and 6-chloropyridazine-3-carboxylic acid (5.0 g, 31.6 mmol) is heated at reflux in acetic acid (50 ml) for 80 hrs. The mixture is cooled and the precipitate which formes is collected to give 4.73 g of crude product, m.p. 253°–300° C. (dec.). Recrystallization of this material from pyridine gives the analytical material, m.p. 260°–262° C.

EXAMPLE 3

10-Oxo-10H-pyridazino(6,1-b)quinazoline-2-carboxylic acid.

A precipitate is obtained when a mixture of methyl anthraniliate (4.78 g, 31.6 mmol), 6-chloropyridazine-3-carboxylic acid (5.0 g, 31.6 mmol) and 50 ml of acetic acid is heated at reflux for 21 hrs; m.p. 246°–50° C. This crude material is recyrstallized from pyridine giving the anlytical sample, m.p. 239°–43° C. (dec.).

EXAMPLE 4

7-Methyl-10-oxo-10H-pyridazino(6,1-b)quinazoline-2-carboxylic acid.

A reaction mixture containing 4-methylanthranilic acid (4.76 g, 31.6 mmol), 6-chloropyridazine-3-carboxylic acid (5.0 g, 31.6 mmol) and 50 ml of glacial acetic is heated at reflux for 67 hrs. The reaction mixture is cooled and the precipitate which formes is collected, m.p. 239°–247° C. (dec.). Recrystallization of the crude material from pyridine gives the analytical sample, m.p. 246°–249° C. (dec.).

We claim:

1. A 10-oxo-10H-pyridazino(6,1-b)quinazoline-2-carboxylic acid having the formula

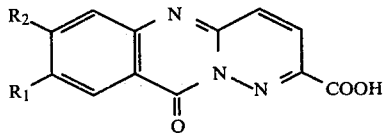

wherein $R_1$ is hydrogen, halogen; $R_2$ is hydrogen, lower alkyl containing one to three carbon atoms, or wherein $R_1$ and $R_2$ taken together with the carbon atoms to which they are attached is a benzo ring, and the pharmaceutically acceptable salts thereof.

2. The compound according to claim 1 which is 7-methyl-10-oxo10H-pyridazino(6,1-b)quinazline-2-carboxylic acid.

3. The compound according to claim 1 which is 8-chloro-10H-pyridazino(6,1-b)quinazoline-2-carboxylic acid.

4. The compound according to claim 1 which is 10-oxo-10H-pyridazino(6,1-b)quinazoline-2-carboxylic acid.

5. The compound according to claim 1 which is 12-xo-12H-benzo(g)pyridazino(6,1-b)quinazoline-2-carboxylic acid.

6. A pharmaceutical composition for the treatment of an allergic reaction in which the active ingredient comprises a compound having the formula according to claim 1 or a pharmaceutically acceptable salt thereof together with any of the conventional pharmaceutically acceptable carriers or excipients.

7. A method of reducing an allergic response in a mammal which comprises the administration of a composition according to claim 6 to a mammal in an effective amount sufficient to inhibit an antibody or antigen reaction in said mammal.

* * * * *